United States Patent [19]

Hsieh

[11] Patent Number: 5,713,883
[45] Date of Patent: Feb. 3, 1998

[54] ABSORBENT ARTICLE HAVING FLEXIBLE BENDING AXES

[75] Inventor: Tong-Ho J. Hsieh, East Brunswick, N.J.

[73] Assignee: McNeil-PPC, Inc., Skillman, N.J.

[21] Appl. No.: 514,169

[22] Filed: Aug. 11, 1995

Related U.S. Application Data

[63] Continuation of Ser. No. 999,322, Dec. 21, 1992, abandoned.

[51] Int. Cl.⁶ ............................................. A61F 13/15
[52] U.S. Cl. ................................. 604/385.1; 604/387
[58] Field of Search ........................... 604/364, 374–377, 604/380–381, 383, 385.1–387, 389, 391

[56] References Cited

U.S. PATENT DOCUMENTS

| 2,064,431 | 12/1936 | Jurgensen | 604/385.1 |
| 3,368,562 | 2/1968 | Vogt | 604/385.1 |
| 3,776,233 | 12/1973 | Schaar | 604/385.1 |
| 3,848,599 | 11/1974 | Schaar | 604/385.1 |
| 3,882,871 | 5/1975 | Taniguchi | 604/385.2 |
| 3,913,578 | 10/1975 | Schaar | 604/385.1 |
| 3,943,930 | 3/1976 | Schaar | 604/385.1 |
| 3,954,107 | 5/1976 | Chesky et al. | 604/385.1 |
| 4,036,233 | 7/1977 | Kozak | 604/385.2 |
| 4,108,179 | 8/1978 | Schaar | 604/385.1 |
| 4,341,216 | 7/1982 | Obenour | 604/383 |
| 4,381,781 | 5/1983 | Sciaraffa et al. | 604/375 |
| 4,425,128 | 1/1984 | Motomura | 604/381 |
| 4,573,990 | 3/1986 | Ohsaki | 604/385.1 |
| 4,605,404 | 8/1986 | Sneider | 604/385.1 |
| 4,701,177 | 10/1987 | Ellis et al. | 604/385 A |
| 4,770,657 | 9/1988 | Ellis et al. | 604/385 A |
| 4,804,380 | 2/1989 | Lassen et al. | 604/385.1 |
| 4,865,597 | 9/1989 | Mason, Jr. et al. | 604/385.1 |
| 4,917,697 | 4/1990 | Osborn, III et al. | 604/389 |
| 4,940,462 | 7/1990 | Salerno | 604/387 |
| 4,944,735 | 7/1990 | Mokry | 604/385.2 |
| 5,009,653 | 4/1991 | Osborn, III | 604/387 |
| 5,062,840 | 11/1991 | Holt et al. | 604/385.1 |

FOREIGN PATENT DOCUMENTS

WO 92/10984   9/1992   WIPO.

Primary Examiner—David H. Willse
Assistant Examiner—K. M. Reichle
Attorney, Agent, or Firm—James P. Barr

[57] ABSTRACT

An absorbent article, such as a sanitary napkin, is provided with first and second flexible bending axes separating front and rear portions of the article from a central portion. Each of the bending axes is created by a notch formed in the longitudinally extending sides of the article. A fluid pervious cover layer forms the body facing surface of the article. A transversely extending slit is formed in the portion of the cover within each of the notches. A fluid impervious barrier layer forms the garment facing surface of the article. A pleat is formed in the portion of the barrier extending between the edges of each of the slits. The notches, slits and pleats allow the front and rear portions of the article to freely bend upward into contact with the use's body and prevent lateral compression in the central portion of the article from being transmitted to the front and rear portions so as to undesirably increase the stiffness of the article in the longitudinal direction.

24 Claims, 4 Drawing Sheets

ABSORBENT ARTICLE HAVING FLEXIBLE BENDING AXES

This is a continuation of application Ser. No. 07/999,322, filed Dec. 21, 1992, now abandoned.

FIELD OF THE INVENTION

The current invention is directed to an absorbent article, such as a sanitary napkin, diaper, incontinence pad or the like. More specifically, the current invention is directed to an absorbent article having a flexible bending axis between at least a front portion of the article and a central portion.

BACKGROUND OF THE INVENTION

Absorbent articles such as sanitary napkins, diapers, incontinence pads and the like typically have an absorbent element that has a fluid pervious body facing surface, adapted to receive body fluid and direct it into the absorbent element for storage, and a fluid impervious garment facing surface that acts as a barrier to body fluid so as to prevent staining of the user's undergarment. In order to ensure that body fluid enters the absorbent, rather than flowing along the surface of the skin and thence to the user's undergarment, it is important to maximize the portion of the body facing surface of the absorbent element that is in contact with the user's body. Thus, the performance of the article depends, in part, on the "fit" of the pad with respect to the user's body.

In the past, absorbent articles have been provided in a flat configuration. The article was fitted to the curved surfaces of the user's body in the perineal area by relying on the panty crotch to raise the front and rear portions of the article relative to the central portion so that the body facing surface of the article more closely matched the surface of the user's body. Consequently, the fit of the article was controlled by its flexibility.

Unfortunately, although absorbent articles are typically fairly flexible in the flat configuration in which the user applies them to the panty, experience has shown that, in actual use, the user's legs compress the central portion of the article so that its thickness, and, therefore, its stiffness in the longitudinal direction, is significantly increased. Although the force from the user's legs is applied directly to only the central portion of the article, the unitized structure of the article causes the deformation to extend into the front and rear portions. Thus, the stiffness is increased throughout the article, preventing the front and rear portions from deflecting upward into body contact.

Another aspect of traditional absorbent articles that detracts from a good fit is the fact that the longitudinal bending of the absorbent article occurs about a neutral axis extending approximately mid-way between the body facing and garment facing surfaces. Thus, the bending places the body facing surface in compression and the garment facing surface in tension. The compression in the body facing surface causes wrinkles that tend to minimize the portion of the body facing surface placed in contact with the body. The tension in the garment facing surface resists the bending and tends to keep the article flat.

Attempts have been made to provide better fitting articles by pre-forming the article so as to impart an arcuate shape in the longitudinal direction. Typically the arcuate shape is created by incorporating elastic elements placed under tension in portions of each of the longitudinally, extending sides of the article—see for example, U.S. Pat. Nos. 4,701,177 (Ellis); 4,770,657 (Ellis); 4,865,597 (Mason) and 4,944,735 (Mokry). In addition, the lateral width of the article has been reduced in its central portion.

Unfortunately, experience has shown that in actual use, the compressive force of the user's legs on the central portion of the article still increases the thickness the article throughout its length, thereby stiffening it in the longitudinal direction and inhibiting the independent motion of the front and rear portions of the article.

Consequently, it would be desirable to provide an absorbent article in which the front and rear portions of the article were capable of freely bending upward into body contact despite the compression of the central portion of the article as a result of pressure from the user's legs.

SUMMARY OF THE INVENTION

It is an object of the current invention to provide an absorbent article in which the front and rear portions of the article were capable of freely bending upward into body contact despite the compression of the central portion of the article as a result of pressure from the user's legs. This object, and other objects, is accomplished in an absorbent product for use in the perineal area of the body to protect the user's undergarment from being stained by body fluid, comprising (i) body facing and garment facing surfaces, (ii) first and second transverse ends, (iii) a first portion disposed adjacent the first transverse end, (iv) a second portion disposed adjacent the first portion, and (v) a first expansion joint formed between the first and second portions.

In one embodiment, the absorbent article further comprises (i) an absorbent element extending through the first and second portions of the article, (ii) a first layer extending between the first and second portions and covering at least a portion of the absorbent element, and (iii) a second layer covering at least and portion of the absorbent element. The first layer is formed from a fluid impervious material and forms the garment facing surface. The second layer is formed from a fluid pervious material and forms the body facing surface. In this embodiment, the first expansion joint comprises (i) a pleat formed in the first layer, (ii) a notch formed in the absorbent element, and (iii) a slit formed in the second layer.

DESCRIPTION OF THE PREFERRED EMBODIMENT

Figure 1:
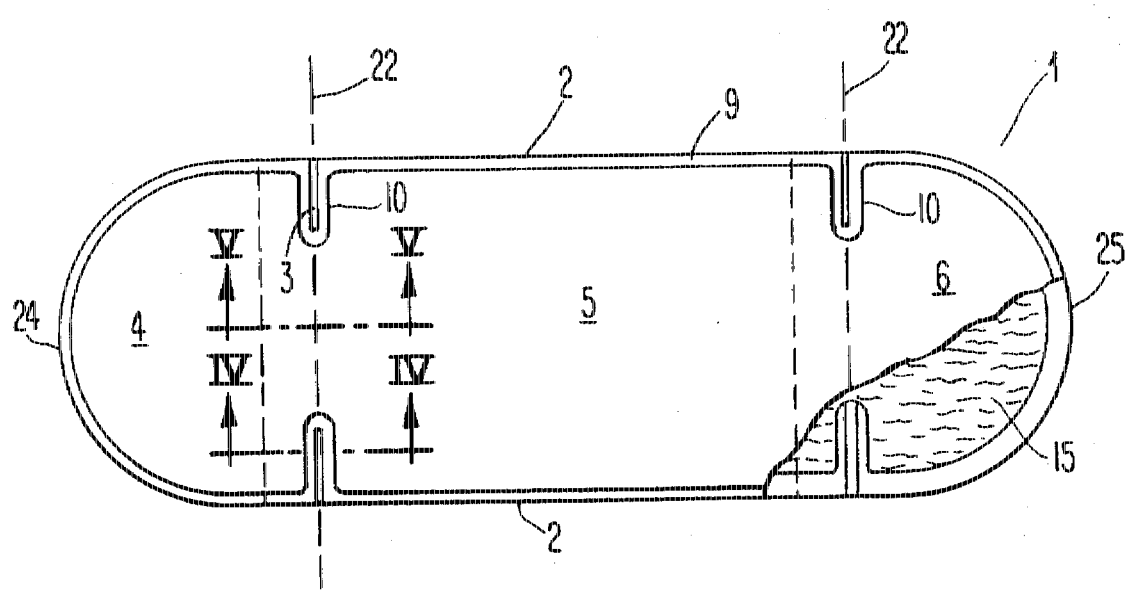
FIG. 1 is a plan view, from above, of a sanitary napkin according to the current invention with a portion of the cover cut away to reveal the absorbent core.
Figure 2:
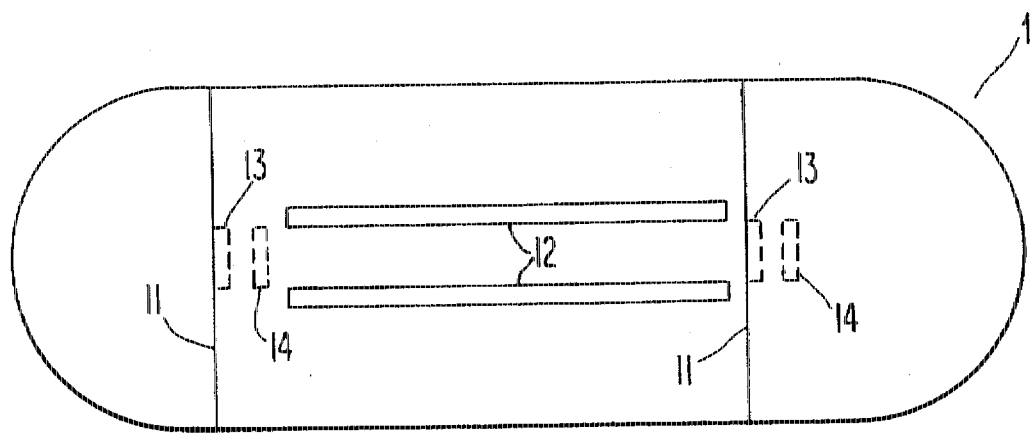
FIG. 2 is a plan view, from below, of the sanitary napkin shown in FIG. 1.
Figure 3:
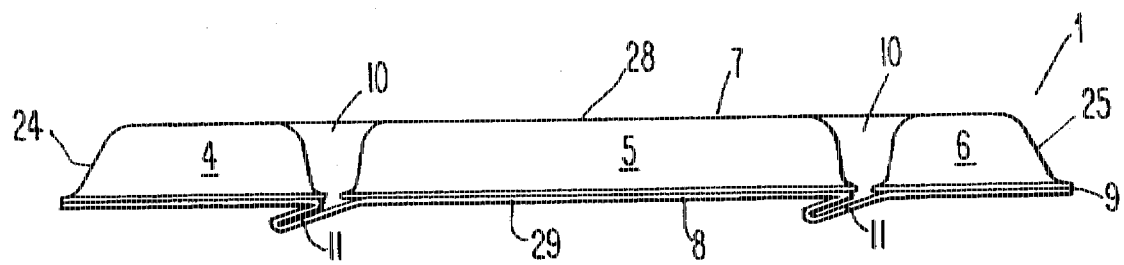
FIG. 3 is an elevation of the sanitary napkin shown in FIG. 1.

A sanitary napkin 1 according to the current invention is shown in FIGS. 1–3. The napkin 1 is comprised of an absorbent element having a body facing surface 28, a garment facing surface 29, left and right longitudinally extending sides 2, a front transverse end 24, and a rear transverse end 25. As shown best in FIGS. 4 and 5, an absorbent core 15 is disposed between the body facing surface 28 and the garment facing surface 29 and extends throughout the length of the napkin 1.

As is known in the art, the absorbent core 15 may be comprised of a loosely associated absorbent hydrophilic material such as cellulose fibers, including wood pulp, regenerated cellulose fibers or cotton fibers, or other absorbent materials generally known in the art, including acrylic fibers, polyvinyl alcohol fibers, peat moss or superabsorbent materials.

The surface 28 of the napkin that is intended to be worn against the body of the user is formed by a layer 7 of a body-fluid pervious material, typically referred to as a "cover." The cover 7 may be formed from any fluid pervious material that is comfortable against the skin and that permits fluid to penetrate to the underlying absorbent core 15, which retains the fluid. The cover 7 should retain little or no fluid in its structure to provide a relatively dry surface next to the skin. The fluid pervious cover 7 may be a fibrous non-woven fabric made of fibers or filaments of polymers such as polyethylene, polypropylene, polyester or cellulose. Alternatively, the cover 7 may be formed from an apertured polymeric film. The thickness of the cover 8 will vary from approximately 0.001 to 0.062 inch, depending on the material chosen.

Generally, the fluid pervious cover 7 is a single sheet of material having a width sufficient to form the body-facing surface 28 of the napkin. Preferably, the fluid pervious cover 7 is longer than the absorbent core 15 so as to form the front and rear transverse ends 24 and 25, respectively, and wider than the absorbent core so as to form the longitudinally extending sides 2.

The napkin 1 further comprises a layer 8 of a body fluid impervious material, typically referred to as a "barrier", that forms the garment facing surface 29. The impervious barrier 8 may comprise any thin, flexible, body fluid impermeable material such as a polymeric film—for example, polyethylene, polypropylene, or cellophane or a normally fluid pervious material that has been treated to be impervious, such as impregnated fluid repellent paper or non-woven fabric material, or a flexible foam, such as polyurethane or cross-linked polyethylene. The thickness of the barrier when formed from a polymeric film is typically only 0.001 to 0.002 inch.

Generally, the barrier 8 is a single sheet of material having a width sufficient to form the garment facing surface 29 of the napkin. As shown in FIGS. 1 and 3, the fluid impervious barrier 8 is joined to the cover 7, for example by an adhesive, around the perimeter of the napkin so as to form flanges 9.

Figure 8:
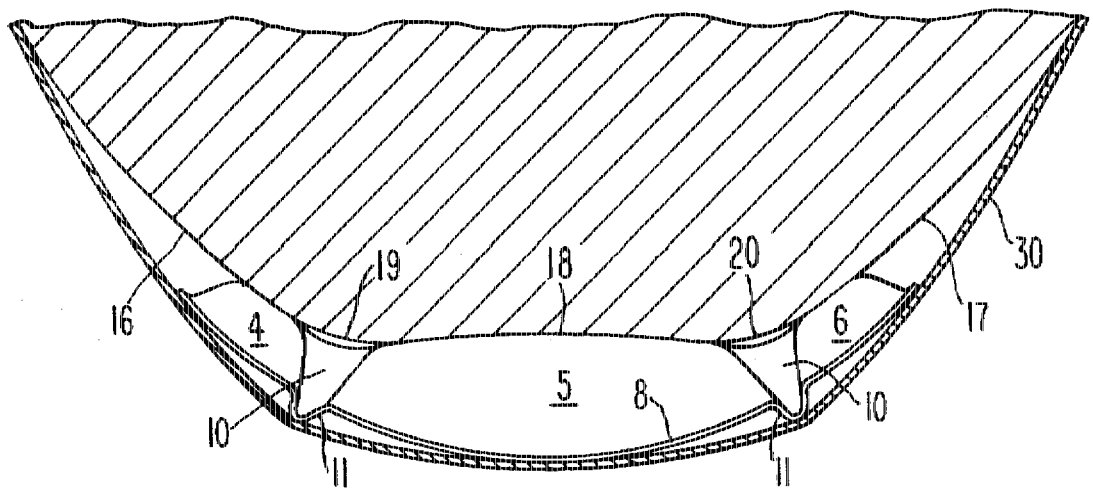
FIG. 8 shows the napkin shown in FIG. 1 in use in the perineal area of a user's body.

The napkin 1 is applied to the crotch of a panty by placing the garment facing surface 29 of the napkin against the inside surface of a panty crotch 30, as shown in FIG. 8. Pressure sensitive adhesive strips 12 are applied to the garment facing surface 29 of the napkin to help maintain the napkin in place, as shown in FIG. 2. As used herein, the term "pressure-sensitive adhesive" refers to any releasable adhesive or releasable tenacious means. Adhesive compositions suitable for sanitary napkins, include, for example, water-based pressure-sensitive adhesives such as acrylate adhesives. Alternatively, the adhesive may comprise rapid setting thermoplastic "hot melt," rubber adhesives or two-sided adhesive tape.

As is customary in the art, a paper release strip (not shown), which has been coated on one side, is applied to protect the adhesive strips 12 prior to use. The coating, which may be silicone, reduces the adherency to the adhesive of the coated side of the release strip. The release strip can be formed from any suitable sheet-like material which, when coated, adheres with sufficient tenacity to the adhesive to remain in place prior to use but which can be readily removed when the napkin is to be used.

As shown in FIGS. 1 and 3, the napkin i has a front portion 4 adjacent the front transverse edge 24, a central portion 5 adjacent the front portion, and a rear portion 6 adjacent the rear transverse edge 25. Although the absorbent core 15 extends through all three portions of the napkin 1, notches 10 formed in the sides of the absorbent core create demarcations that separate the front and rear portions 4 and 6, respectively, from the central portion 5. Each notch 10 is formed by bonding, for example using adhesive, the cover 7 directly to the barrier 8 along a line extending transversely inward from the side 2 of the napkin 1 so that the flange 9 created by the cover 7 and barrier 8 extends into the notch 10. This bonding creates a trough into which the absorbent core 15 does not extend, thereby reducing the lateral thickness of the absorbent core 15 in the vicinity of the notches 10.

Figure 7:
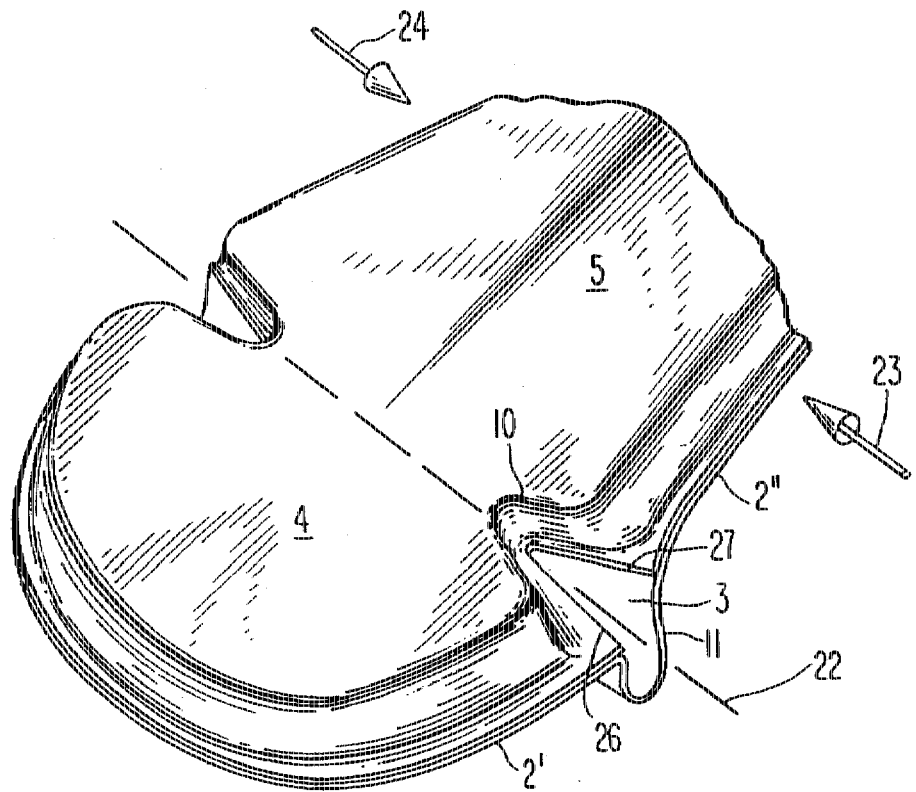
FIG. 7 is similar to FIG. 6 except showing the napkin when the central portion is being laterally compressed.

The notches 10 serve to locally weaken the napkin 1 so as to create preferential bending axes 22, shown in FIGS. 1 and 7. The bending axes 22 facilitate the upward bending of the front and rear portion 4 and 6, respectively, of the napkin so that they may be more easily placed into contact with the user's body by the panty 30, as shown in FIG. 8. The length of each of the portions 4, 5 and 6 are selected so that the panty 30 can readily bend the front and rear portions 4 and 6, respectively, into intimate contact with the front and rear portions of the user's body in the perineal area. Specifically, as shown in FIG. 8, the front bending axis 22, created by the notches 10 separating the front portion 4 from the central portion 5, is disposed proximate the front point of inflection 19 in the curvature of the user's body where the convex curvature of the frontal body region 16 intersects with the concave curvature of the perineum 18. In addition, the rear bending axis 22, created by the notches 10 separating the rear portion 6 from the central portion 5, is disposed proximate the rear point of inflection 20 in the curvature of the user's body where the convex curvature in the rear body region 17 intersects with the concave curvature in the perineum 18.

In the preferred embodiment, the front portion 4 is approximately 2.5 to 4.5 inches long, preferably approximately 3 inches, the central portion 5 is approximately 3.5 to 4.5 inches long, preferably approximately 3.5 inches, and the rear portion 6 is approximately 2 to 4 inches long, preferably approximately 2.5 inches.

In addition to creating preferred bending axes 22, the notches 10 tend to isolate the front and rear portions 4 and 6, respectively, from the central portion 5 of the napkin 1 so that lateral compression of the central portion by the user's legs does not significantly increase the thickness of the napkin in the vicinity of the bending axes 22. Such thickening would increase the stiffness of the napkin in the longitudinal direction and impede bending. In this respect, the notches 10 act as expansion joints since they allow the portions of the sides 2 of the napkin in the central portion 5, to which the compressive force is applied, to move independently from the portions of the sides 2 in the front portion 4 of the napkin, as discussed further below.

Figure 4:
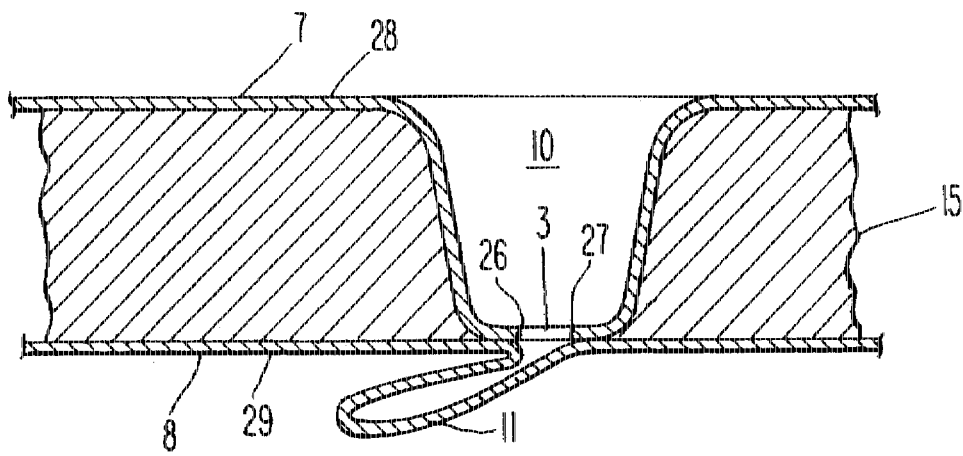
FIG. 4 is a cross-section taken through lines IV—IV shown in FIG. 1.
Figure 5:
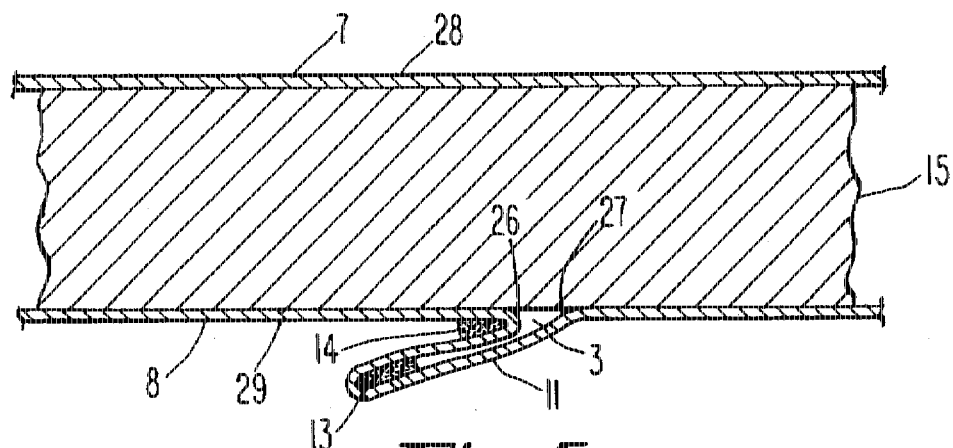
FIG. 5 is a cross-section taken through lines V—V shown in FIG. 1.

According to an important aspect of the current invention, the formation of expansion joints along each of the bending axes 22 that isolate the motion of the front and rear portions of the napkin from the central portion is further enhanced by the creation of slits 3 in the cover 7 and pleats 11 in the barrier, as shown best in FIGS. 4 and 5. Each slit 3 is formed in the portion of the cover 7 disposed within the notch 10 by making a transversely extending cut in the cover. In the preferred embodiment, each slit 3 extends inward approximately 0.5 inch from the side 2 of the napkin.

Each pleat 11 is formed in the portion of the barrier 8 that extends between the forward and rear edges 26 and 27, respectively, of the slit 3. The pleats 11 extend transversely across the width of the napkin from one longitudinal side 2 to the other, as shown in FIG. 2. In the preferred embodiment, the length of each pleat 11 from its base to its tip is approximately 0.25 to 0.75 inch. The pleat 11 is formed by folding a portion of the barrier over onto itself. As shown in FIGS. 2 and 5, the pleat 11 is maintained in the barrier 8 by means of strips of adhesive 13 and 14 disposed along the longitudinal centerline of the napkin. Adhesive strip 13 keeps the tip of the pleat 11 together and adhesive strip 14 secures the base of the pleat to the remaining portion of the barrier 8. In the preferred embodiment, the strips of adhesive 13 and 14 are approximately 0.5 to 1.25 inch long—that is, as measured in the transverse direction of the napkin—and approximately 0.25 to 0.75 inch wide. Alternatively, the pleats 11 could be thermally formed in the barrier 8.

Figure 6:
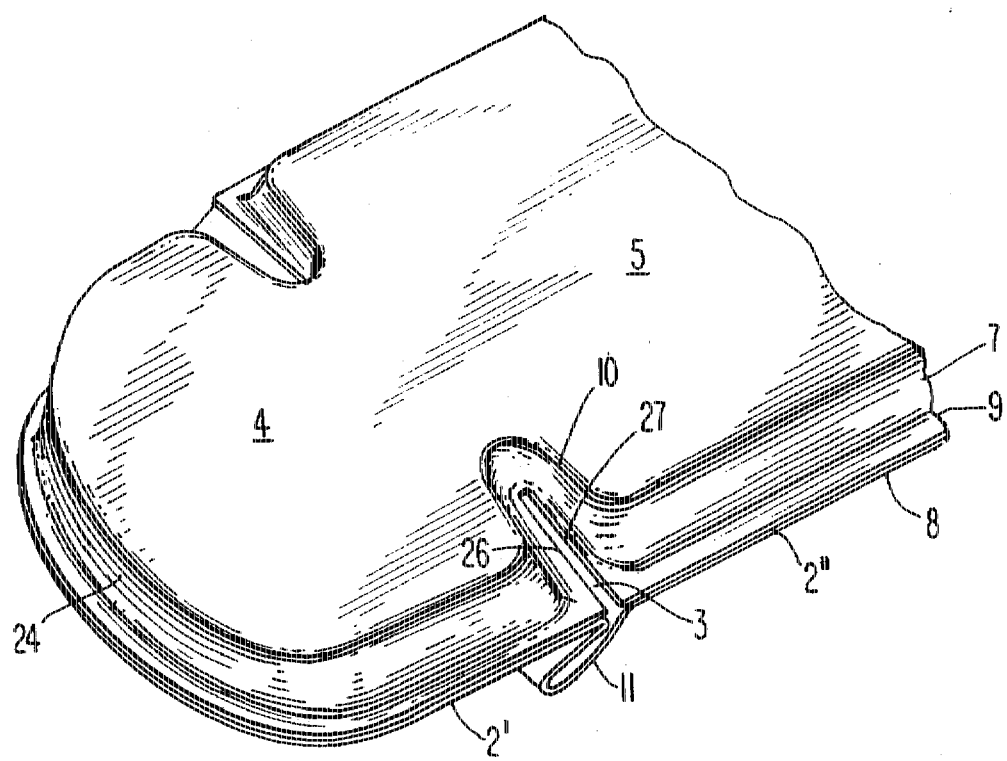
FIG. 6 is a detailed isometric view of the portion of the sanitary napkin shown in FIG. 1 between the front and central portions when the napkin is in its undeformed state.

As shown in FIGS. 6 and 7, in use, the user's legs apply opposing forces 23 and 23' to the portions 2" of the longitudinal sides 2 in the central portion 5 of the napkin. The forces 23 and 23' laterally compress the central portion 5. This lateral compression increases the thickness of the central portion 5, as shown in FIG. 8. However, as a result of the expansions joints, the front portion 4 remains substantially isolated from the central portion 5 so that deformation of the central portion does not result in substantial thickening of the portion of the absorbent core 15 that extends through the bending axis 22. As a result, the front portion 4 is free to move independently of the central portion 5 so that it can be readily bent upward about axis 22 into contact with the convex curved surface in the frontal portion 16 of the user's body, as shown in FIG. 8. A similar situation occurs at the rear portion 6 of the article.

As shown in FIG. 7, the front portion 4 is isolated from the central portion 5 because the notch 10 and the slit 3 in the cover 7 allows the portion 2" of the longitudinally extending side in the central portion of the napkin to move independently of the portion 2' of the longitudinally extending side in the front portion. As a result, the deformation of side 2" is not transmitted to side 2'. As can be seen, the slit 3, and to some extent the notch 10, opens up in response to the lateral compression of the central portion 5 so that the rear edge 27 of the slit rotates rearward to accommodate the deformation along the side 2", leaving the forward edge 26 of the slit essentially undisturbed. Thus, as a result of the notch 10 and slit 3, the cover 7 and absorbent core 15, although they extend through all three portions of the napkin, do not transmit deformation in the central portion 5 to either the front or rear portions 4 and 6, respectively.

Similarly, the pleats 11 in the barrier 8 ensure that, despite that fact that the barrier extends through all three portions of the napkin, it does not transmit deformation from the central portion to the front or rear portions. As shown in FIG. 7, when the side 2" is compressed and the rear edge 27 of the slit 3 rotates rearward, the pleat 11 is partially unfolded allowing it to absorb the movement in the portion of the barrier 8 in the central portion 5 without pulling on the portion of the barrier in the front portion of the napkin 4.

Thus, the pleats 11 act as expansion joints that allow the barrier 8 to locally expand and thereby isolate the movement of the barrier in the central portion from that in the front and rear portions. Forming pleats 11 in the barrier 8 is preferable to forming slits, as is done in the cover 7, since they provide a barrier to body fluid that leaks out the notch, thereby preventing the fluid from staining the panty.

As can be seen, the expansion joints allow the flexibility of the napkin 1 to be maintained despite the lateral compression in the central portion 5 so that the panty 30 can cause the front and rear portions to bend upward so that the napkin conforms to the surface of the user's body, as shown in FIG. 8.

Moreover, by allowing the napkin to bend along localized axes 22, rather than imparting an arcuate curvature to the entire napkin, less undesirable wrinkling occurs in the body facing surface 28. Lastly, in addition to acting as expansion joints at the longitudinal sides 2 of the napkin when the central portion is compressed, the expansion of the pleats 11 across the entire width of the napkin ensures that the barrier is not placed in tension, thereby resisting bending, when the front and rear portions 4 and 6, respectively, bend upward into body contact.

Figure 9:
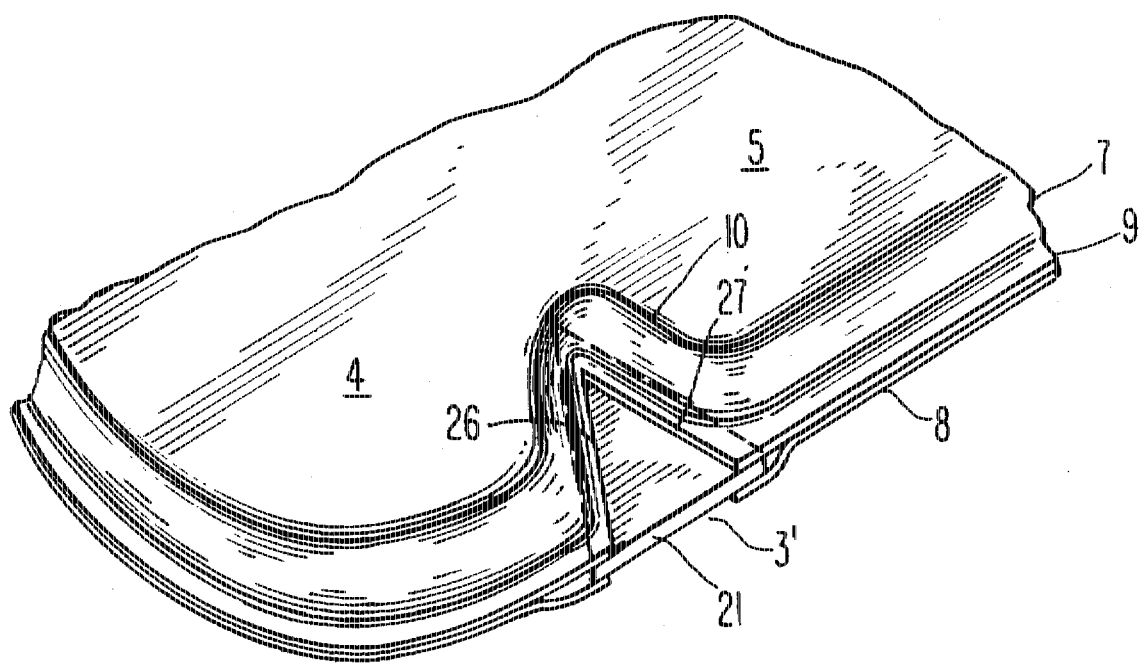
FIG. 9 is a view similar to FIG. 6 showing an alternate embodiment of the current invention.

FIG. 9 shows another embodiment of the current invention. In this embodiment, a V-shaped wedges of elastic material 21 extend across V-shaped slits 3" formed in both the cover 7 and the barrier 8 at each of the four notch 10 locations. The wedges 21 act as expansion joints since their elasticity accommodates the motion of the longitudinally extending sides 2" in the central portion 4 of the napkin so that deformation in the central portion is not transmitted to the front and rear portions. In addition, the wedge 21 may be attached to the cover and barrier while in tension so that, when released, the wedge tends to bend the front and rear portions upward into a pre-formed shape.

Although the current invention has been described with reference to a sanitary napkin, the invention is also applicable to other absorbent products, such as sanitary napkins, panty liners, diapers and incontinence pads. Consequently, the present invention may be embodied in other specific forms without departing from the spirit or essential attributes thereof and, accordingly, reference should be made to the appended claims, rather than to the foregoing specification, as indicating the scope of the invention.

What is claimed:

1. An absorbent product for use in a perineal area of a body to protect a user's undergarment from being stained by body fluid, comprising:

a) an absorbent element having first and second transverse ends and forming first and second absorbent portions disposed between said first and second transverse ends, a transversely extending bending axis formed in said absorbent element between said first and second absorbent portions;

b) a first expansion joint formed between said first and second absorbent portions and located along said bending axis;

c) a first layer covering at least a portion of said absorbent element and forming a garment facing surface, said first layer extending between said first and second absorbent portions, said first expansion joint comprising a transversely extending pleat formed in said first layer;

d) a second layer covering at least a portion of said absorbent element, said second layer formed from a fluid pervious material and forming a body facing surface, the first layer is joined to said second layer adjacent a peripheral edge margin of the absorbent product and the absorbent element is positioned between said first layer and said second layer and wherein said first expansion joint further comprises a transversely extending slit formed in said second layer.

2. The absorbent article according to claim 1, wherein said first absorbent portion is disposed adjacent said first transverse end and said second absorbent portion is disposed adjacent said first absorbent portion.

3. The absorbent article according to claim 1, wherein said absorbent element extends through said first and second absorbent portions, and wherein said expansion joint further comprises means for locally weakening said absorbent element.

4. The absorbent article according to claim 3, wherein said local weakening means comprises a notch formed in said absorbent element.

5. The absorbent article according to claim 1, wherein said first layer is formed from a fluid impervious material.

6. The absorbent article according to claim 1, wherein said expansion joint further comprises a notch formed in said absorbent element between said first and second portions.

7. An absorbent product for use in a perineal area of a body to protect a user's undergarment from being stained by body fluid, comprising:
   a) an absorbent element having first and second transverse ends and forming first and second absorbent portions disposed between said first and second transverse ends, said first and second absorbent portions each having first and second longitudinal sides;
   b) a first expansion joint formed between said first and second absorbent portions, said first expansion joint extending between said first longitudinal sides of said first and second absorbent portions;
   c) a first layer covering at least a portion of said absorbent element and forming a garment facing surface, said first layer extending between said first and second absorbent portions, said first expansion joint comprising a pleat formed in said first layer; and
   d) a second layer covering at least a portion of said absorbent element, said second layer formed from a fluid pervious material and forming a body facing surface, the first layer is joined to said second layer adjacent a peripheral edge margin of the absorbent product and the absorbent element is positioned between said first layer and said second layer and wherein said first expansion joint further comprises a slit formed in said second layer.

8. The absorbent article according to claim 7, further comprising a second expansion joint, said second expansion joint extending between said second longitudinal sides of said first and second portions.

9. The absorbent article according to claim 8, further comprising:
   a) a third absorbent portion disposed between said second transverse end and said second portion, whereby said second portion is a central portion, said third portion having first and second longitudinal sides;
   b) a third expansion joint formed between said first longitudinal sides of said second and third portions; and
   c) a fourth expansion joint formed between said second longitudinal sides of said second and third portions, respectively.

10. An absorbent product for use in a perineal area of a body to protect a user's undergarment from being stained by body fluid, comprising:

a) an absorbent element having first and second transverse ends and forming first and second absorbent portions disposed between said first and second transverse ends;
   b) a first expansion joint formed between said first and second absorbent portions;
   c) a first layer covering at least a portion of said absorbent element and forming a garment facing surface, said first layer extending between said first and second absorbent portions, said first expansion joint comprising a pleat formed in said first layer;
   d) a second layer covering at least a portion of said absorbent element and having first and second longitudinal edges, said second layer formed from a fluid pervious material and forming a body facing surface, the first layer is joined to the second layer adjacent a peripheral edge margin of the absorbent product and the absorbent element is positioned between said first layer and said second layer and wherein said first expansion joint further comprises a slit formed in said second layer, and wherein said slit extends transversely from said first longitudinal edge toward said second longitudinal edge.

11. An absorbent product for use in a perineal area of a body to protect a user's undergarment from being stained by body fluid, comprising:
   a) an absorbent element having first and second transverse ends and forming first and second absorbent portions disposed between said first and second transverse ends;
   b) a first expansion joint formed between said first and second absorbent portions;
   c) a first layer covering at least a portion of said absorbent element and forming a garment facing surface, said first layer extending between said first and second absorbent portions, said first expansion joint comprising a pleat formed in said first layer, wherein said pleat extends transversely across said first layer; and
   d) a second layer covering at least a portion of said absorbent element, said second layer formed from a fluid pervious material and forming a body facing surface, the first layer is joined to said second layer adjacent a peripheral edge margin of the absorbent product and the absorbent element is positioned between said first layer and said second layer and wherein said first expansion joint further comprises a slit formed in said second layer.

12. The absorbent article according to claim 11, wherein said first layer has first and second longitudinal edges, and wherein said pleat extends transversely across said first layer from said first longitudinal edge to said second longitudinal edge.

13. An absorbent product for use in a perineal area of a body, comprising:
   a) an absorbent element having first and second transverse ends and front and central portions, said front portion disposed adjacent said first transverse end and said central portion disposed adjacent said front portion and wherein said absorbent element has first and second longitudinally extending sides;
   b) first and second layers of materials each of which covers at least a portion of said absorbent element and the first layer is joined to the second layer adjacent a peripheral edge margin of the absorbent product and wherein the absorbent element is positioned between said first layer and said second layer; and
   c) means for allowing said central portion of said absorbent element to compress laterally inward independently of said front portion comprising:

i) first and second transversely extending notches formed in said first and second longitudinally extending sides of said absorbent element, respectively;

ii) a transversely extending pleat formed in said first layer, at least a portion of said pleat being disposed in said first and second transversely extending notches, respectively; and iii) first and second transversely extending slits formed in said second layer and disposed in said first and second transversely extending notches, respectively.

14. The absorbent article according to claim 13 wherein said first layer of material is fluid impervious and forms a garment facing surface.

15. The absorbent article according to claim 13, wherein said second layer of material is fluid pervious and forms a body facing surface.

16. An absorbent product for use in a perineal area of a body, comprising:

a) an absorbent element having first and second longitudinally extending sides and first and second transverse ends, a first portion of said absorbent element disposed adjacent said first transverse end and a second portion of said absorbent element disposed adjacent said first portion;

b) a first layer of a fluid impervious material, a first portion of said fluid impervious layer at least partially covering said first portion of said absorbent element, a second portion of said fluid impervious layer at least partially covering said second portion of said absorbent element;

c) a bending axis formed in said absorbent element between said first and second portions thereof;

d) a pleat formed in a third portion of said fluid impervious layer extending between said first and second portions of said fluid impervious layer;

e) a second layer of fluid pervious material at least partially covering said first and second portions of said absorbent element and the first layer is joined to the second layer adjacent a peripheral edge margin of the absorbent product and wherein the absorbent element is positioned between said fluid impervious layer and said fluid pervious layer; and f) first and second substantially transversely extending slits formed in said fluid pervious layer at each of said first and second longitudinal sides of said absorbent element, respectively, each of said slits having first and second edges, at least a portion of said pleat extending between said first and second edges of each of said first and second slits.

17. The absorbent article according to claim 16, wherein said pleat extends transversely between said first and second longitudinal sides.

18. The absorbent article according to claim 17, wherein said bending axis is formed by locally weakening said absorbent element.

19. The absorbent article according to claim 18, wherein said bending axis is formed by first and second notches disposed in said first and second longitudinal extending sides, respectively.

20. An absorbent product for use in a perineal area of a human body to protect a user's undergarment from being stained by body fluid, comprising:

a) an absorbent element having first and second transverse ends and first, second, and third absorbent portions, wherein the first absorbent portion is disposed adjacent the first transverse end and the second absorbent portion is disposed adjacent the first absorbent portion and wherein the third absorbent portion is disposed adjacent the second transverse end and the second portion, a first bending axis formed between said first and second absorbent portions and a second bending axis formed between said second and third absorbent portions;

b) first and second layers of material, each of said layers covering at least a portion of said first, second and third absorbent portions and the first layer is joined to the second layer adjacent a peripheral edge margin of the absorbent product and wherein the absorbent element is positioned between said first and second layers of material; and c) first, second, third, and fourth expansion joints wherein the first and second expansion joints are formed between the first and second portions and the third and fourth expansion joints are formed between the second and third portions, each of said expansion joints comprising:

(i) a transversely extending slit formed in said first layer of material, and (ii) at least a portion of a transversely extending pleat formed in said second layer of material.

21. The absorbent article according to claim 20, wherein the first and second absorbent portions each have first and second longitudinal sides, and wherein the first expansion joint extends between the first longitudinal sides of the first and second absorbent portions.

22. The absorbent article according to claim 21, wherein the second expansion joint extends between the second longitudinal sides of the first and second absorbent portions.

23. The absorbent article according to claim 22, wherein the third absorbent portion has first and second longitudinal sides, and wherein the third expansion joint extends between the first longitudinal sides of the second and third absorbent portions.

24. The absorbent article according to claim 23, wherein the fourth expansion joint extends between the second longitudinal sides of the second and third absorbent portions.

\* \* \* \* \*